United States Patent [19]

Hargreaves

[11] Patent Number: 5,328,910
[45] Date of Patent: Jul. 12, 1994

[54] SINO-ATRIAL NODE MODULATING PYRROLOPYRIMIDINES

[75] Inventor: Rodney B. Hargreaves, Poynton, England

[73] Assignee: Imperial Chemical Industries PLC, London, England

[21] Appl. No.: 777,982

[22] Filed: Oct. 17, 1991

[30] Foreign Application Priority Data

Oct. 18, 1990 [GB] United Kingdom ............. 9022644.0

[51] Int. Cl.$^5$ .................. A61K 31/505; C07D 487/02
[52] U.S. Cl. ..................................... 514/258; 544/280
[58] Field of Search ........................ 514/258; 544/280

[56] References Cited

U.S. PATENT DOCUMENTS

| | | | |
|---|---|---|---|
| 2,748,124 | 5/1956 | Burtner et al. | 544/323 |
| 4,229,453 | 10/1980 | Roth et al. | 514/258 |
| 4,339,453 | 7/1982 | Grier et al. | 514/259 |
| 4,503,050 | 3/1985 | Wade | 514/228.5 |
| 4,725,600 | 2/1988 | Takaya et al. | 514/269 |

FOREIGN PATENT DOCUMENTS

| | | |
|---|---|---|
| 0168262 | 1/1986 | European Pat. Off. . |
| 0322133 | 6/1989 | European Pat. Off. . |
| 0390112 | 10/1990 | European Pat. Off. . |
| 0434341 | 6/1991 | European Pat. Off. . |
| 1241832 | 6/1967 | Fed. Rep. of Germany . |
| 2818676 | 11/1979 | Fed. Rep. of Germany . |
| 3145287 | 5/1983 | Fed. Rep. of Germany . |
| WO90/12790 | 11/1990 | PCT Int'l Appl. . |
| 0658205 | 10/1951 | United Kingdom . |
| 0815833 | 7/1959 | United Kingdom . |
| 1020306 | 2/1966 | United Kingdom . |

OTHER PUBLICATIONS

Chemical Abstracts 101(3) 23425k (1984) Abstract of Joergensen et al., Chemica Scripta (1984) 23(2) 73-79.

(List continued on next page.)

*Primary Examiner*—Mukund J. Shah
*Assistant Examiner*—Matthew V. Grumbling
*Attorney, Agent, or Firm*—Cushman, Darby & Cushman

[57] ABSTRACT

This invention concerns novel heterocyclic compounds of formula I (and pharmaceutically-acceptable salts thereof):

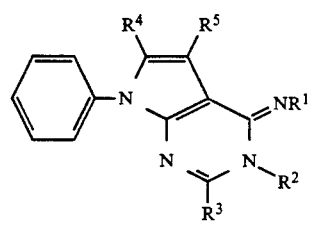

wherein: $R^1$ is hydrogen, (1-8C)alkyl or phenyl(1-4C)alkyl; $R^2$ is (1-6)alkyl, phenyl(1-4C) alkyl, (3-6C)cycloalkyl, (3-6C) cycloalkyl(1-4C)alkyl, (3-6C)cycloalkyl, phenyl(1-4C)alkyl, (3-6C)cycloalkyl, (3-6C)cycloalkyl(1-4C)alkyl, phenyl or (3-6C)alkenyl; $R^4$ and $R^5$ are independently selected from hydrogen and (1-6C)alkyl; and wherein the phenyl ring and/or one or more of said phenyl or benzene moieties may optionally be unsubstituted or substituted by one or more substituents independently selected from halogeno, (1-4C)alkyl, (3-6C)alkenyl, (1-4C)alkoxy, cyano, trifluoromethyl, nitro, carboxy, (1-4C)alkylamino, dialkylamino of up to six carbon atoms, (1-4C)alkylthion, (1-4C)alkylsulphinyl, (1-4C)alkylsulphonyl and (1-4C)alkylsulphonyl and (1-4C)alkylenedioxy; but excluding the compound in which $R^1$, $R^3$, $R^4$ and $R^5$ are each methyl, the phenyl ring is unsubstituted and $R^2$ is ethyl, and its pharmaceutically-acceptable salt. The compound of formula I (and pharmaceutically-acceptable salts thereof) possess beneficial effects on the cardiovascular system, and in particular beneficial effects modulated via the sino-atrial node. Also included are processes for the manufacture of compounds of the formula I (or a pharmaceutically-acceptable salt), and pharmaceutical compositions.

10 Claims, No Drawings

OTHER PUBLICATIONS

Denny et al., "Potential Antitumor Agents. 29. Quantitative Structure–Activity Relationships for the Antileukemic Bisquaternary Ammonium Heterocycles" *J. Med. Chem.*, (1979) 22, No. 2, 134–50.

Suyama et al. "Preparation of 1-Phenyl-Polyhydro-s-–Triazines" *Org. Syn, Chem.*, (1976) 34 No. 6, 417–424; English Translation (Chemical Abstracts, 86, No. 9, Abstr. No. 55393m).

Csuros et al., "Acylation of Disubstituted Cyanamides with Phosgene. III. Reactions of 1,3,5-trichloro-2,-4-diazapentadiene derivatives with amines" *Chemical Abstracts*, (Jan. 7, 1974) 80, No. 1, Abstr. No. 3471s.

Csuros et al., "Acylation of Disubstituted Cyanamides with Phosgene. IV. Reactions of 1,3,5-Trichloro-2,-4-diazapentadiene Derivatives with Amines" *Chemical Abstracts*, (Jan. 7, 1974) 80, No. 1, Abstr. No. 3472t.

E. W. Parnell, "N,N'-Dipyrimidinylalkylenediamines and Related Compounds" *Chemical Abstracts*, (Jan. 21, 1963) 58, No. 2, Abstr. No. 1451e.

Tamada et al., "Preparation of Benzoheterocycle Derivatives as Drugs for Treating Heart Diseases" *Chemical Abstracts*, (Oct. 23, 1989) 111, No. 17, Abstr. No. 153834k.

Muravich-Aleksandr et al., "Dihydropurines. IV. Alkylation and Isomerization of 6–dialkylaminopurine Derivatives" *Chemical Abstracts*, (Oct. 29, 1973) 79, No. 17, Abstr. No. 105194a.

Kazantseva et al., "Reactions of N-alkylazinium Cations. 3. Pteridinium salts. Synthesis, structure and reaction with simple nucleophiles" *Chemical Abstracts*, (Oct. 13, 1986) 105, No. 15. Abstr. No. 133849s.

Weinstock et al., "Pteridines. VI. Preparation of Some 6–Aryl-7–aminopteridines" *Chemical Abstracts*, (Oct. 21, 1968) 69, No. 17, Abstr. No. 67335f.

Jorgensen et al., "Phosphorus Pentoxide in Organic Synthesis VIII. Synthesis of 3-aryl-7-phenyl-3,7-dihydro-4H-pyrrolo[2,3-d]pyrimidin-4-imines" *Chemica Scripta*, (1984) 23, No. 2, 73-79.

Hilmy et al., "Phosphorus Pentoxide in Organic Synthesis XXXIII. Novel route for synthesis of 3,7-dihydro-4H-pyrrolo-[2,3-d]pyrimidin-4-ones" *chemica Scripta*, (1988) 28, 303–305.

Jorgensen et al., "Phosphorus Pentoxide in Organic Synthesis XIII. Synthesis of 7-phenyl-7H-pyrrolo[2-,3-d]pyrimidine-4-amines" *Chemica Scripta*, (1984) 24, 73-79.

Girgis e4t al., "Phosphorus Pentoxide in Organic Synthesis XI. A New Synthetic Approach to 7-Deazahypoxanthines" *Synthesis* (Communications), (1984) 101-104.

SINO-ATRIAL NODE MODULATING PYRROLOPYRIMIDINES

This invention relates to novel heterocyclic compounds and, more particularly, novel pyrrolo[2,3-d]pyrimidine derivatives which possess beneficial effects on the cardiovascular system, pharmaceutical compositions containing such a derivative as active ingredient, and processes for the manufacture of and medical use of the said derivatives.

Although numerous compounds are known to have medically useful effects on the cardiovascular system, there is a need for agents which modulate the action of the sino-atrial node in warm-blooded animals such as man in a beneficial, selective and medically useful manner so that the agents are useful in treating cardiovascular disorders associated with an inappropriately elevated heart rate (that is by having a bradycardic effect) and yet have minimal effects on other haemodynamic parameters such as blood pressure or cardiac output. It is an object of the invention to provide such an agent which has inter alia bradycardic properties.

Certain pyrimidine derivatives which are able to modulate the action of the sino-atrial node are reported in EP 434,341 and EP 422,178.

Pyrrolo[2,3-d]pyrimidine derivatives which are not substituted on either of the ring nitrogen atoms of the pyrimidine moiety are known. For example, a synthetic route to N-aryl-7-phenyl-7H-pyrrolo[2,3-d]pyrimidin-4-amines is described by Girgis et al (Chemica Scripta, 24, 73-79, 1984); 7-phenyl-pyrrolo[2,3-d]pyrimidine derivatives are described as possessing analgesic, sedative, anti-convulsant and inflammatory activity in published German patent application Ser. No. 3,145,287; and 5,6-dimethyl-pyrrolo[2,3-d]pyrimidine derivatives are reported to be useful as analgesics, anti-inflammatory agents and CNS depressants in published German patent application Ser. No. 2,818,676.

According to the present invention there is provided a compound of formula I (set out hereinafter together with the other chemical formulae referred to herein), or a pharmaceutically-acceptable salt thereof, wherein: $R^1$ is hydrogen, (1–8C)alkyl or phenyl(1–4C)alkyl; $R^2$ is (1–6C)alkyl, phenyl(1–4C)alkyl, (3–6C)cycloalkyl, (3–6C)cycloalkyl(1–4C)alkyl or phenyl; $R^3$ is hydrogen, (1–6C)alkyl, phenyl(1–4C)alkyl, (3–6C)cycloalkyl, (3–6C)cycloalkyl(1–4C)alkyl, phenyl or (3–6C)alkenyl; $R^4$ and $R^5$ are independently selected from hydrogen and (1–6C)alkyl; and wherein the phenyl ring and/or one or more of said phenyl or benzene moieties may optionally be unsubstituted or substituted by one or more substituents independently selected from halogeno, (1–4C)alkyl, (3–6C)alkenyl, (1–4C)alkoxy, cyano, trifluoromethyl, nitro, carboxy, (1–4C)alkylamino, dialkylamino of up to six carbon atoms, (1–4C)alkylthio, (1–4C)alkylsulphinyl, (1–4C)alkylsulphonyl and (1–4C)alkylenedioxy; but excluding the compound in which $R^1$, $R^3$, $R^4$ and $R^5$ are each methyl the phenyl ring is unsubstituted and $R^2$ is ethyl, and its pharmaceutically-acceptable salt.

Within the specification it is to be understood that generic terms such as (1–6C)alkyl encompass both the straight chain and branched form.

It will also be understood that when one of the substituents in the formula I compounds contains a chiral centre, the compounds of the invention may exist in, and be isolated in, optically active or racemic form. It will also be understood that the compounds of formula I and their salts may exist in another tautomeric form to that depicted in formula I, or in a mixture of more than one possible tautomeric forms. The invention includes any tautomeric, optically active or racemic from of a compound of formula I which possesses the afore-mentioned beneficial pharmacological effects.

A particular value for $R^1$ when it is alkyl is, for example, (1–6C)alkyl, such as methyl, ethyl, propyl, isopropyl, butyl, isobutyl, sec-butyl, pentyl or hexyl; more particularly (1–4C)alkyl such as methyl, ethyl, propyl, isopropyl, butyl, iso-butyl or sec-butyl, of which methyl is generally preferred.

A particular value for $R^1$ when it is phenylalkyl is, for example, benzyl, 1-phenylethyl or 2-phenylethyl, of which benzyl is generally preferred.

Particular values for $R^2$ when it is alkyl include (1–4C)alkyl, such as methyl, ethyl, propyl, isopropyl, butyl, isobutyl or sec-butyl, of which methyl is generally preferred.

A particular value for $R^2$ when it is (3–6C)cycloalkyl-(1–4C)alkyl is, for example, (3–6C)cycloalkyl(1–2C)alkyl for example cyclopropylmethyl, cyclopropylethyl, cyclobutylmethyl, cyclobutylethyl, cyclopentylmethyl, cyclopentylethyl, cyclohexylmethyl or cyclohexylethyl.

A particular value for $R^2$ when it is phenylalkyl is, for example, benzyl, 1-phenylethyl or 2-phenylethyl, of which benzyl is generally preferred.

A particular value for $R^2$ when it is cycloalkyl is, for example, cyclopropyl, cyclobutyl, cyclopentyl or cyclohexyl.

A particular value for $R^3$ when it is alkyl is, for example, (1–4C)alkyl, for example, methyl, ethyl, propyl, isopropyl, butyl, isobutyl or sec-butyl.

A particular value for $R^3$ when it is phenylalkyl is, for example, benzyl, 1-phenylethyl or 2-phenylethyl.

A particular value for $R^3$ when it is cycloalkyl is, for example, cyclopropyl, cyclobutyl, cyclopentyl or cyclohexyl.

A particular value for $R^3$ when it is (3–6C)cycloalkyl-(1–4C)alkyl is, for example, (3–6C)cycloalk cyclopropylmethyl, cyclopropylethyl, cyclobutylmethyl, cyclobutylethyl, cyclopentylmethyl, cyclopentylethyl, cyclohexylmethyl or cyclohexylethyl.

A particular value for $R^3$ when it is alkenyl is, for example, allyl, but-2-enyl, but-3-enyl, 2-methyl-2-propenyl or pentenyl.

A particular value for $R^4$ and $R^5$ when they are alkyl is, for example, (1–4C)alkyl such as methyl, ethyl, propyl, isopropyl, butyl, isobutyl or sec-butyl.

Conveniently, the phenyl ring is unsustituted or bears one or two substituents, and more conveniently the phenyl ring is unsustituted.

Conveniently, the phenyl or benzene moiety present in $R^2$ or $R^3$ is unsustituted or bears one or two substituents, and more conveniently the phenyl ring or benzene moiety is unsustituted.

Particular values for optional substituents (defined above) which may be present on the phenyl ring or a phenyl or benzene moiety include, by way of example:
for halogeno, fluoro, chloro and bromo;
or alkyl, methyl, ethyl and propyl;
for alkenyl, allyl and 2-methyl-2-propenyl;
for alkoxy, methoxy, ethoxy and propoxy;
or alkylamino, methylamino and ethylamino;
for dialkylamino, dimethylamino and diethylamino;
for alkylthio, methylthio and ethylthio;

for alkylsulphinyl, methylsulphinyl and ethylsulphinyl; for alkylsulphonyl, methylsulphonyl and ethylsulphonyl; and for alkylenedioxy, methylenedioxy and isopropylidenedioxy.

It is generally preferred that R1 is alkyl, especially methyl.

It is generally preferred that $R^2$ is alkyl, especially methyl.

It is generally preferred that $R^3$ is alkyl, especially methyl.

It is generally preferred that $R^4$ and $R^5$ are independently selected from hydrogen and methyl.

Specific values for $R^1$ include, for example, hydrogen, methyl ethyl propyl and hexyl; for $R^2$ methyl; for $R^3$ hydrogen and methyl; for $R^4$, hydrogen and methyl.

In one embodiment of the present invention $R^1$ is (1–6C)alkyl or benzyl; $R^2$ is (1–6C)alkyl, (3–6C)cycloalkyl(1–4C)alkyl, or benzyl; $R^3$ is (1–6C)alkyl; $R^4$, $R^5$ are independently selected from hydrogen and (1–4C)alkyl; and wherein the phenyl ring and/or the phenyl moiety of the benzyl group is unsubstituted or is substituted by one or more substituents independently selected from halogeno, (1–4C)alkyl, (3–6C)alkenyl, (1–4C)alkoxy, cyano, trifluoromethyl, nitro, carboxy, (1–4C)alkylamino, dialkylamino of up to six carbon atoms, (1–4C)alkylthio, (1–4C)alkylsulphinyl, (1–4C)alkylsulphonyl and (1–4C)alkylenedioxy.

Particular and preferred values are the appropriate values given above.

Conveniently, $R^1$ is (1–6C)alkyl, $R^2$ is (1–4C)alkyl, $R^3$ is (1–6C)alkyl, $R^4$ and $R^5$ are independently selected from hydrogen and (1–4C)alkyl, and the phenyl ring is unsubstituted or is substituted by one, two, or three substituents independently selected from halogeno, (1–4C)alkyl, (3–6C)alkenyl, (1–4C)alkoxy, cyano, trifluoromethyl, nitro, carboxy, (1–4C)alkylamino, dialkylamino of up to six carbon atoms, (1–4C)alkylthio, (1–4C)alkylsulphinyl, (1–4C)alkylsulphonyl and (1–4C)alkylenedioxy.

It is generally preferred that $R^1$, $R^2$ and $R^3$ are each methyl.

A group of compounds which are of particular interest comprises those compounds of formula I, or a pharmaceutically-acceptable salt thereof, wherein:

$R^1$ is hydrogen, (1–8C)alkyl or phenyl(1–4C)alkyl;

$R^2$ is methyl;

$R^3$ is hydrogen, (1–6C)alkyl, phenyl(1–4C)alkyl, (3–6C)cycloalkyl, (3–6C)cycloalkyl(1–4C)alkyl, phenyl or (3–6C)alkenyl;

$R^4$ and $R^5$ are indepentently selected from hydrogen and (1–6C)alkyl; and wherein the phenyl ring and/or one or more of said phenyl or benzene moieties may optionally be unsubstituted or substituted by one or more substituents independently selected from halogeno, (1–4C)alkyl, (3–6C)alkenyl, (1–4C)alkoxy, cyano, trifluoromethyl, nitro, carboxy, (1–4C)alkylamino, dialkylamino of up to six carbon atoms, (1–4C)alkylthio, (1–4C)alkylsulphinyl, (1–4C)alkylsulphonyl and (1–4C)alkylsulphonyl and (1–4C)alkylenedioxy.

Particular and preferred values for the various groups are the appropriate values defined above.

A further group of compounds of particular interest are those of formula I, or a pharmaceutically-acceptable salt thereof, wherein:

$R^1$ is hydrogen or (1–6C)alkyl;

$R^2$ is (1–4C)alkyl (especially methyl);

$R^3$ is hydrogen or (1–4C)alkyl;

$R^4$ and $R^5$ are independently selected from hydrogen and (1–4C)alkyl (especially methyl); and wherein the phenyl ring may optionally be unsubstituted or substituted by one or two substituents independently selected from halogeno (such as fluro, chloro or bromo), (1–4C)alkyl (such as methyl), and (1–4C)alkoxy (such as methoxy); but excluding the compound and its pharmaceutically-acceptable salts, in which $R^1$, $R^3$, $R^4$ and $R^5$ are each methyl and $R^2$ is ethyl Particular values are the appropriate values defined above.

Compounds which are of particular interest include the compounds described in the accompanying Examples and are are provided as a further feature of the present invention. Thus the present invention also provides a compound of formula I which is selected from:

2,3-dimethyl-4-methylimino-7-phenyl-3H,7H-pyrrolo[2,3-d]pyrimidine;

2,3,5,6-tetramethyl-4-methylimino-7-phenyl-3H,7H-pyrrolo-[2,3-d]pyrimidine;

2,3,5,6-tetramethyl-4-imino-7-phenyl-3H,7H-pyrrolo-[2,3-d]pyrimidine;

2,3,5,6-tetramethyl-4-7-propylimino-7-phenyl-3H,7H-pyrrolo-[2,3-d]pyrimidine;

2,3,5,6-tetramethyl-4-ethylimino-7-phenyl-3H,7H-pyrrolo-[2,3-pyrimidine;

2,3,5,6-tetramethyl-4-n-hexylimino-7-phenyl-3H,7H-pyrrolo-[2,3-d]pyrimidine;

3,5,6-trimethyl-4-imino-7-phenyl-3H,7H-pyrrolo-[2,3-d]pyrimidine;

or a pharmaceutically-acceptable salt thereof.

The present invention includes salts of the compounds of formula I, and hence the present invention encompasses quaternary pyrimidinium salts of the compounds of formula I. Suitable salts include those prepared by reaction of a compound of formula I with an acid which affords a physiologically acceptable counter anion ($Y^-$), for example, halide (such as chloride, bromide or iodide), sulphate, nitrate, and trifluoroacetic.

The compounds of the invention may be obtained by standard procedures of organic chemistry already known to be applicable to the preparation of structurally analogous compounds, for example those procedures described in standard reference works and on the chemistry of the heterocycles and reviews of the chemistry of pyrrolopyrimidines (see for example Synthesis, 1974, 837). Such procedures for the manufacture of the novel compounds of formula I are provided as a further feature of the invention and are illustrated by the following preferred processes in which the various generic radicals have any of the meanings defined hereinbefore:-

(a) A compound of formula II (in which the phenyl ring is optionally substituted) is reacted with an alkylating agent.

In formula II, the various groups $R^1$, $R^3$, $R^4$ and $R^5$ may take any of the meanings defined above for the compounds of formula I, and the phenyl ring may optionally be substituted.

Suitable alkylating agents include compounds of the formula $R^2Z$, wherein Z is a suitable leaving group. A preferred value of Z is, for example, halide (especially iodide, bromide or chloride), sulphate and p-toluenesulphonate. In the case where $R^2$ is a methyl group, the alkylating agent is preferably dimethyl sulphate.

The reaction is generally carried out by heating the alkylating agent with the compound of formula II, at a temperature of, for example, 40°-120° C. and is conveniently carried out in a suitable solvent, for example, in an ether such as dioxane, tetrahydrofuran or t-butyl methyl ether.

The compounds of formula II (in which the phenyl ring is optionally substituted), particularly when $R^3$ and $R^4$ are hydrogen, may be prepared, for example, by the route shown in Scheme A. Suitable reaction conditions for the various stages are indicated in Scheme A, and in Example 1 of the accompanying examples.

The compounds of formula II may also be prepared by the reaction of a compound of formula VII (in which the phenyl ring is optionally substituted) with phosphorous oxychloride and then the appropriate amine of formula $R^1NH_2$ using, for example, similar conditions to those described below for the conversion of compounds of formula V to those of formula I. Compounds of formula II may also be prepared by heating a compound of formula VII in a mixture of phosphorous pentoxide, N,N-dimethylcyclohexylamine and the appropriate amine hydrochloride of formula $R^1NH_3+Cl^-$ (as described by Girgis et al, Chemica Scripta, 24, 73-79, 1984). Compounds of formula VII may be prepared by heating a compound of formula III (in which the phenyl ring is optionally substituted) in a mixture of phosphorous pentoxide, N,N-dimethylcyclohexylamine and water (as described by Girgis et al, Synthesis, 1984, 101-104).

The compounds of formula II (in which the phenyl ring is optionally substituted) may also be prepared using the method of K M H Hilmy, J. Mogensen, and E.B. Pedersen reported in Chemica Scripta 1988, 28, 303-305; that is by heating a compound of formula III in which the phenyl ring is optionally substituted in a mixture of phosphorous pentoxide, N,N-dimethyicyclohexylamine hydrochloride, the appropriate amine hydrochloride and water. The compound of formula VII produced may then be reacted with the phosphorous oxychloride and then appropriate amine of formula $R^1NH_2$.

(b) A pyrimidinium salt of the formula IV (in which the phenyl ring is optionally substituted) wherein X is a suitable leaving group is reacted with an amine of the formula $R^1NH_2$.

In formula IV, the various groups $R^2$, $R^3$, $R^4$ and $R^5$ may take any of the meanings defined above for the compounds of formula I, and the phenyl ring may optionally be substituted. The group W represents an appropriate counter ion.

The process is generally carried out at an elevated temperature in the range, for example, 20°-150° C. and in the presence of a suitable solvent or diluent such as a (1-4C)alkanol or N,N-dimethylformamide.

A particularly suitable leaving group X is, for example, halogeno (especially chloro or bromo), dichlorophosphinoyl [—O.PO.Cl$_2$], or dibromophosphinoyl [-O.PO.Br$_2$]. The latter two groups may conveniently be introduced in situ by the reaction of the corresponding pyrimidinone, that is a compound of formula V, with phosphorus oxychloride or oxybromide, respectively.

Conveniently, the compound of formula V is heated in excess phosphorous oxychloride or oxybromide as appropriate, and the excess reagent is removed, for example by evaporation, before reaction with the amine of formula $R^1NH_2$.

It is preferred that a compound of formula V is reacted with phosphorous oxychloride, conveniently with heating, followed by an amine of formula $R^1NH_2$.

The pyrimidinones of formula V may be obtained by standard procedures, for example using the route illustrated in Scheme B. Suitable reaction conditions for the various stages are indicated in Scheme B, and in Example 3 of the accompanying Examples.

The pyrimidinones of formula V may also be obtained by reaction of a compound of formula VII with a compound of formula $R^2Z$ in which Z is a suitable leaving group, such as chloride. For example, a compound of formula VII may be reacted with a compound of formula $R^2Z$ (for example an alkyl iodide) in the presence of a base such as potassium hydroxide, in a suitable sovent such as ethanol.

When the compound of I is obtained as a base and a salt is required, the base form may be conveniently be reacted with the appropriate acid of formula H.Y. It will be appreciated that the counter anion $Y^-$ in the salts of compounds of formula I may readily be changed, for example, by reaction compound with a suitable salt such as a silver salt or by ion-exchange chromatography on a column of a basic macroreticular resin in the form of its salt with the desired counter anion, or another conventional method.

When the non-ionic base form of a compound of I is required, it may be obtained from a salt of a compound of formula I, for example, by reaction with a macroreticular resin containing quaternary ammonium hydroxide groups. The process is conveniently carried out by exposing a solution of the salt of the compound of formula I in an aqueous solvent such as an aqueous (1-4C)alkanol (for example methanol, ethanol or 2-propanol) to the resin at or near ambient temperature, for example by trickling the solution over a bed or through a column of the resin. The base form may then conveniently be returned to the salt form by recation with the appropriate acid of formula H.Y.

It will also be appreciated that certain of the various optional substituents in the compounds of the invention may be introduced by standard aromatic substitution reactions or generated by conventional functional group modifications either prior to or immediately following process (a) or (b) above, and as such are included in the process aspect of the invention. Such reactions and modifications include, for example, introduction of nitro or halogeno, reductive alkylation of nitro, oxidation of alkylthio to alkylsulphinyl or alkylsulphonyl and reduction of alkynyl or alkenyl. The reagents and reaction conditions for such procedures are well known in the chemical art.

Many of the chemical intermediates referred to herein are novel and are accordingly provided as further features of the present invention. Thus the present invention also provides, for example, a compounds of formula VI (wherein the phenyl ring is optionally sustituted as defined above and $R^1$, $R^2$, $R^3$, $R^4$ and $R^5$ are as defined above), a compound of formula II (wherein the phenyl ring is optionally sustituted as defined above and $R^1$, $R^3$, $R^4$ and $R^5$ are as defined above), and a compound of formula IV (wherein the phenyl ring is optionally sustituted as defined above and $R^2$, $R^3$, $R^4$ and $R^5$ are as defined above).

The compounds of the present invention possess useful pharmacological properties, and hence the present invention also provides a compound of formula I (as herein defined), or a pharmaceutically-acceptable salt thereof, for use in therapy.

As indicated above, the compounds of the invention possess useful pharmacological properties and modulate the action of the sino-atrial node in warm-blooded animals in a beneficial, selective and medically useful manner so that the agents are useful in treating cardiovascular disorders associated with an inappropriately elevated heart rate and with minimal effects on other haemodynamic parameters such as blood pressure or cardiac output.

Thus, according to the present invention there is also provided the use of a compound of formula I (as herein defined), or a pharmaceutically-acceptable salt thereof, in the manufacture of a medicament for treating cardiovascular disorders in warm-blooded mammals, such as man.

The beneficial and selective effects of the cardiovascular system may be demonstrated using one or more of the following standard laboratory techniques. a) Bradycardic effect (reduction in beating rate of the spontaneously beating isolated guinea pig right atrium).

This technique involves the dissection of the right atrium from a guinea pig heart, taking care not to damage the sino-atrial node region. The atrium is established in oxygenated (95% $O_2$; 5% $CO_2$) Tyrode's solution [containing 8.0g NaCl, 0.19g KCl, 0.025g $MgCl_2$, 0.05g $NaH_2PO_4$, 1.0g $NaHCO_3$, 0.2g $CaCl_2$ and 2.7g glucose, per liter of deionised water] between two platinum spikes which are connected via an amplifier to a conventional rate-meter, triggered by the action potentials across the atrium. The preparation is bathed in oxygenated Tyrode's solution at 37 degrees Celsius and allowed to equilibrate for 30 minutes before the addition of a solution of the test compound in a mixture of dimethyl sulphoxide and Cremophor EL, diluted as required with Tyrode's solution. Further solutions of test compound are then added cumulatively at 15 minute intervals or when a steady-state beating rate has been attained. This enables an $IC_{20}$ (i.e. the micromolar concentration required to reduce the beating rate by 20%) to be calculated. Typically, a compound of formula I will have an $IC_{20}$ of 10 micromolar or less.

b) Effect on contractile force of electrically stimulated isolated guinea pig left atrium.

This technique involves the dissection of the left atrium from a guinea pig heart into oxygenated Tyrode's solution. The atrium is then clamped in a polyacrylate plastic holder containing two stainless steel stimulating electrodes. The free end of the atrium (normally the atrial appendage) is attached with silk thread to an isometric force transducer. The atrium is then set under a resting tension of 1g and is allowed to equilibrate in oxygenated Tyrode's solution for 20 minutes before being stimulated into beating by application of 2.5 Hz, 3 mS pulses at 1.5 times the threshold voltage (normally in the range 3-7 V). A solution ($10^{-5}$ M or less) of the test compound [made up essentially as in (a) above, but using physiological saline solution in place of Tyrode's solution] is then added and the effect on contractile force measured. In this way a comparison of the effect with that of a control solution without any test compound can be obtained. Typically, at a concentration in the range 1-30 micromolar compounds of the formula I show <15% reduction in contractile force.

c) Bradycardic effect in the anaesthetised rat

This technique involves the use of Wistar rats (Alderley Park strain) which are pre-anaesthetised by intravenous injection of alphaxalone/alphadalone (1.5ml per kg). A polyethylene cannula is inserted into the jugular vein and anaesthesia is maintained by infusion of alphaxalone/alphadalone at a rate of 0.025-0.12 ml per kg per minute. A polyethylene cannula is also inserted into the carotid artery and connected to a pressure transducer filled with physiological saline solution. The arterial blood pressure signal is used to trigger an internally calibrated heart rate meter and the transducer is calibrated with a mercury manometer. The output of the heart rate meter and of the pressure transducer are then recorded simultaneously on a standard chart recorder. After cannulation, the rat preparation is allowed to stabilise for 10 minutes. A solution of a test compound [made up as in (a) above, in a volume of 1ml per kg] is then administered via the venous cannula in four cumulative doses separated by 5 minute intervals. A group of five rats is used for each test compound. The effects on heart rate and blood pressure may then be determined in comparison with those of a control injection.

Typically, a compound of formula I active using this procedure will require an i.v. dose of 5 mg/kg or less to produce a 30% reduction in heart rate (i.e. the $ED_{30}$ dose).

The beneficial effects of a test compound on the cardiovascular system, such as bradycardic effects without an adverse effect on heart force, blood pressure and or cardiac output, may also be determined in anaesthetised dogs and in dogs in which tachycardia has been induced by exercise. In general, the compounds of the invention show significant and predominantly selective bradycardic effects as evidenced by activity in at least two of the above mentioned test techniques. No overt toxicity is generally observed with the compounds of formula I in the above in vivo test techniques at doses several multiples of those at which significant bradycardic effects are seen.

By way of illustration, the compound described hereinafter in Example 1 had an $IC_{20}$ of $<1\times10^{-6}$M in procedure (a) and had an $ED_{30}$ of 1.2mg/kg i.v. for reduction of heart rate in procedure (c). Other compounds of formula I exemplified hereinafter will in general show activity of the same general order.

When used in the treatment of diseases of the cardiovascular system, such as myocardial ischaemia affecting warm-blooded animals (and in particular man), it is envisaged that a compound of formula I will be administered orally, intravenously or by some other medically acceptable route (such as by inhalation, insufflation, sub-lingual or transdermal means) so that a dose in the general range, for example, 0.01 mg to 10 mg per kg body weight is received. However, it will be hnderstood that the precise dose administered will necessarily vary according to the nature and severity of the disease and the age and sex of the patient being treated.

In general, the compounds of formula I (or the related pyrimidinium salts) will usually be administered in the form of a pharmaceutical composition, that is, together with a pharmaceutically acceptable diluent or carrier. Thus, the present invention also provides a pharmaceutical composition which comprises a compound of formula I (as herein defined), or a pharmaceutically-acceptable salt thereof, in association with a pharmaceutically-acceptable diluent or carrier.

A composition of the invention may be in a variety of dosage forms. For example, it may be in the form of tablets, capsules, solutions or suspensions for oral administration; in the form of a suppository for rectal administration; in the form of a sterile solution or suspension for administration by intravenous or intramuscular injection; in the form of an aerosol or a nebuliser solution or suspension, for administration by inhalation; in the form of a powder, together with pharmaceutically acceptable inert solid diluents such as lactose, for administration by insufflation; or in the form of a skin patch for transdermal administration. The compositions may conveniently be in unit dose form containing, for example, 5–200 mg of the compound of formula I.

A composition may be obtained by conventional procedures using pharmaceutically acceptable diluents and carriers well known in the art. Tablets and capsules for oral administration may conveniently be formed with a coating, such as an enteric coating (for example, one based on cellulose acetate phthalate) to minimise dissolution of the active ingredient of formula I in the stomach or to mask unpleasant taste.

The compositions of the invention may also contain one or more agents known to be of value in the diseases or conditions of the cardiovasculature intended to be treated. Thus, they may contain, in addition to the compound of formula I, for example, one or more other known agents selected from platelet aggregation inhibitors, prostanoid constrictor antagonists or synthase inhibitors (such as thromboxane $A_2$antagonists or synthase inhibitors), cyclooxygenase inhibitors, hypolipidemic agents, anti-hypertensive agents (such as an angiotensin converting enzyme inhibitors, renin inhibitors or angiotensin antagonists), inotropic agents, $\beta$-adrenergic antagonists, thrombolytic agents, vasodilators and calcium channel antagonists.

In addition to their use in therapeutic medicine, the compounds of formula I are also useful as pharmacological tools in the development and standardisation of test systems for the evaluation of the new cardiovascular agents in laboratory animals such as cats, dogs, rabbits, monkeys, rats and mice.

The invention will now be illustrated by the following non-limiting Examples in which, unless otherwise stated:-

(i) evaporations were carried out by rotary evaporation in vacuo;
(ii) operations were carried out at room temperature, that is in the range 18°–26° C.;
(iii) flash column chromatography was performed on silica gel (Merck Kieselgel Art. 9385, obtained from E Merck, Darmstadt, Germany);
(iv) yields are given for illustration only and are not necessarily the maximum attainable by diligent process development;
(v) proton NMR spectra were normally determined at 200 MHz in deuterated chloroformas solvent, using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d,doublet;
(vi) all end-products were characterised by microanalysis, melting point (m.p.) and NMR; and
(vii) conventional abbreviations are used for individual radicals and recrystallisation solvents, for example, Me=methyl, Et=ethyl, Pr=Propyl, $Pr^i$=isopropyl, Bu=butyl, $Bu^i$=isobutyl, Ph=phenyl; EtOAc=ethyl acetate, $Et_2O$=ether, MeCN=acetonitrile, MeOH=methanol, EtOH=ethanol, $Pr^iOH$=2-propanol, $H_2O$=water.

EXAMPLE 1

2,3-dimethyl-4-methylimino-7-phenyl-3H,7H-pyrrolo-[2,3-d] pyrimidine

A mixture of 2-methyl-4-methylamino-7-phenyl-7H-pyrrolo-[2,3-d] pyrimidine (0.5g, 2.1mM) and dioxan (15ml) was heated under reflux for 18 hours. The mixture was cooled and then the solvent was removed by evaporation. The residue was purified by flash chromatography on ICN neutral alumina (32–63) using methylene chloride which contained an increasing amount of methanol (up to a maximum of 5%) as eluant to give a solid. This solid was recrystallised from hexane to give 2,3-dimethyl-4-methylimino-7-phenyl-3H,7H-pyrrolo[2,3-d] pyrimidine as a white solid (126mg), m p. 160–161° C; microanalysis, found: C, 71 2; H,5 9; N,22.0%; $C_{14}H_{14}N_4$ requires C,71.4; H, 6.3; N, 22.2%; NMR: 2.48(3H,s,C-CH$_3$), 3.48 (3H,s,N-CH$_3$), 3.56(3H,s,N-CH$_3$), 6.90(1H,d,CH), 6.97(1H,d,CH), 7.34(1H, complex, aromatic), 7.47(2H, complex, aromatic), 7.60(1H, complex, aromatic).

[Note: the site of alkylation was confirmed by conventional Nuclear Overhauser studies].

The starting material was prepared as follows:- a) A mixture of triethyl-1,1,2-ethanetricarboxylate (20ml, 87mM) and acetamidine hydrochloride (8.22g, 87mM) was added to a solution of sodium methoxide (9.4g, 174mM) in dry methanol (100ml). The mixture was heated at 90° C. for 15 hours. The solvent was evaporated and the residue dissolved in water (150ml). The pH of the solution was adjusted to pH6 using concentrated hydrochloric acid. The resultant precipitate was collected by filtration, washed with water and then acetone, to give 4,6-dihydroxy-2-methylpyrimidine-5-acetic acid, methyl ester as a white solid (11.85g, 68.8%), m.p. >270° C.; microanalysis, found: C,48.5; H, 5.1; N, 14.1%; C7HSN2O4 requires C, 48.3; H,5.1; N, 13.8%; NMR: NaOD; 2.45(3H, s, pyrimidine-CH$_3$), 3.57(2H,s,CH$_2$), 3.87(3H,s,OCH$_3$).

b) A mixture of 4,6-dihydroxy-2-methylpyrimidine-5-acetic acid, methyl ester (10.5g, 53mM) and phosphorus oxychloride (52ml, an excess) was heated under reflux for two hours. The excess phosphorus oxychloride was removed by distillation under reduced pressure and the residue dissolved in methylene chloride (75ml). This solution was tipped cautiously into cold water (200ml) and the layers separated. The aqueous phase was extracted with methylene chloride (2×50ml). The organic extracts were combined, dried, and the solvent was evaporated to give crude 4,6-dichloro-2-methylpyrimidine-5-acetic acid, methyl ester (10.32g, 82%) which was used without purification for the next synthetic stage. A sample of crude material (obtained from a repeat preparation) was purified by flash column chromatography to yield a solid with m.p. 67°–68° C.; microanalysis, found; C,40.9; H, 3.2; N, 11.7%; $C_2H_8N_2Cl_2O_2$ requires C,40.9; H,3.4; N, 11.9%; NMR: 2.7(3H,s,pyrimidine-CH$_3$), 3.76(3H,s,OCH$_3$), 3.94(2H,s,CH$_2$).

c) A mixture of 4,6-dichloro-2-methylpyrimidine-5-acetic acid, methyl ester (8.5g, 36mM) and aniline (4.7g, 49mM) was heated at 50° C. for 13 hours. Methylene chloride (300ml) was added to the cooled mixture and the mixture filtered. The liltrate was washed with 2M hydrochloric acid (1×170ml, 1×85ml) and water. The organic layer was separated, stirred with 2M sodium hydroxide (110ml) and then separated. The aqueous layer was extracted with methylene chloride (2×85ml). The organic layers were combined, washed with water, over anhydrous magnesium sulphate and the solvent evaporated to afford a solid. This solid was purified by flash column chromatography on silica (Merck 9385), eluting with ethyl acetate/hexane (20:80 v/v) to give 4-anilino-6-chloro-2-methylpyrimidine-5-acetic acid, methyl ester (3.92g, 48.6%), m.p. 115°-116° C.; microanalysis, found; C,57.7; H, 4.5; N, 14.2%; C14H14N3O2. requires C, 57.6; H, 4.8; N, 14.4%; NMR: 2.53(3H,s,2-CH$_3$), 3.79(3H,s, COOCH$_3$), 3.80(2H,s,CH$_2$), 7.05–7.65(5H, complex, aromatic), 7.9–8.0 (1H, broad,-N—H).

d) A mixture of 4-anilino-6-chloro-2-methylpyrimidine-5-acetic acid, methyl ester (5.0g, 17.2mM) and benzylmethylamine (2.22ml, 17.2mM) was heated at 160° C. for 3.5 hours. The mixture was cooled and then partitioned between methylene chloride (50ml) and 2M hydrochloric acid (50ml). The organic layer was separated, washed with a solution of sodium hydroxide (2M, 50ml), water, dried and the solvent evaporated. The residue was purified by flash column chromatography on silica (Merck 9385), eluting with ethyl acetate/hexane (20:80, v/v) to give 4-(N-benzylmethylamino)-2-methyl-6-oxo-7-phenyl-5,6-dihydro-7H-pyrrolo[2,3-d]pyrimidine (2.64g, 44.6%) m.p. 81°-84° C.; microanalysis, found; C, 73.0; H, 6.0; N, 16.3%; C$_{21}$H$_{20}$H$_{4}$O requires C, 73.3; H, 5.8; N, 16.3%; NMR: DMSOd$_6$: 2.3(3H, s, pyrimidine-CH$_3$), 3.2(3H,s,N-CH$_3$), 3.95(2H,s,COCH$_2$), 4.85(2H,s,N-CH$_2$), 7.2–7.55(10H, complex, aromatic).

e) A solution of 1M BH$_3$.THF complex in tetrahydrofuran (10.4ml, 9.2mM) was added dropwise, under an atmosphere of argon, to a stirred mixture of 4-(benzylmethylamino)-2-methyl-6-oxo-7-phenyl-5, 6-dihydro-7H-pyrrolo-[2,3-d]-pyrimidine (1.6g, 4.6mM) in dry tetrahydrofuran (105ml). The mixture was stirred at ambient temperature for 24 hours. The mixture was then added to 2M hydrochloric acid (100ml), the pH was adjusted to about pH7 using concentrated sodium hydroxide and then extracted with ethyl acetate (2×200ml). The organic layers were combined, dried and the solvent evaporated. The residue was purified by flash column chromotography on silica (Merck 9385), using a mixture of methylene chloride: hexane: ethyl acetate (10:8:1) as eluant to give 4[N-benzylmethylamino)-2-methyl-7-phenyl-5,6-dihydro-7H-pyrrolo-[2,3-d]-pyrimidine in the form of a pure solid with m.p. 105°-106° C.; microanalysis, found; C, 75.5; H, 6.7; N, 16.8%; C$_{21}$H$_{22}$N$_4$.0.2H$_2$requires C, 75.6; H, 6.9; N, 16.8%. NMR: 2.47(3H,s,pyrimidine-CH$_3$), 3.14(3H,s,N—CH$_3$), 3.21(2H,t,N—CH$_2$—CH$_2$—), 3.91(2H,t,N—CH2—CH2—), 4.18(2H,s,N—CH2Ph), 6.99(1H,t,aromatic), 7.23–7.47(7H, complex, aromatic), 7.73(2H,d,aromatic); and a crude solid. The material was combined and used without further purification in the subsequent stage of the synthesis.

A mixture of 4[N-benzylmethylamino)-2-methyl-7-phenyl-5,6-dihydro-7H-pyrrolo[2,3-d]pyrimidine from a repeat preparation (3.84g), ammonium formate (4.5g, approximately 2 Mol equivalents), 10% palladium on charcoal (0.38g) and absolute ethanol (150ml) was stirred at ambient temperature for 5 minutes and then heated under reflux for 22 hours. The mixture was cooled and the catalyst removed by filtration through diatomaceous earth. The filtrate was concentrated by evaporation of the volatile material, and the residue was purified by flash. column chromatography on silica (Merck 9385) using ethyl acetate/hexane (20:80 v/v) followed by methanol/methylene chloride (5:95 v/v) as elutant to give a colourless syrup (1.73g) which was used without further purification in the subsequent stage of the synthesis.

A mixture of the colourless syrup (1.73g), 30% palladium on charcoal (0.17g) and diphenyl ether (5ml) was heated under reflux for 15 minutes. The mixture was cooled. The catalyst was removed by filtration through diatomaceous earth and the filtrate concentrated by evaporation of volatile materials to afford a solid. This solid was purified by recrystallisation from ethyl acetate/hexane (1:1 v/v) to give 2-methyl-4-methylamino-7-phenyl-7H-pyrrolo-[2,3-d]pyrimidine (1.37g) m.p 202°-203° C. microanalysis, found: C, 70 5; H, 5 9; N, 23.4%; C$_{14}$H$_{14}$N$_4$ requires: C, 70.6; H, 5.8; N, 23.5%; NMR: 2.49(3H,s,pyrimidine-CH3), 3.07(3H d,NHCH3), 6.72(1H,d N—CH=CH—) 7.24(1M,d,N—CH=CH—), 7.30(1M,t,aromatic), 7.2–7.3(1H, broad, NH), 7.48(2H,t,aromatic), 7.88(2H,d,aromatic).

EXAMPLE 2

2,3-dimethyl4-methylimino-7-phenyl-3H,7H-pyrrolo[2,3-d] pyrimidine hydrochloride Hydrogen chloride gas was passed into a solution of 2,3-dimethyl-4-methylimino-7-phenyl-3H,7H-pyrrolo[2,3-d] pyrimidine in hexane to give a precipitate. The precipitate was collected by filtration and dried to afford 2,3-dimethyl-4-methylimino-7-phenyl-3H,7H-pyrrolo[2,3-d] pyrimidine hydrochloride as a solid, mp 257°-258° C.

EXAMPLE 3

A mixture of 2,3,5,6-tetramethyl-7-phenyl-3H,7H-pyrrolo-[2,3-d]pyrimidin-4-one (0.4 g, 1.5 mM) and phosphorous oxychloride (3 ml) was heated at 95° C. for three hours. The mixture was cooled and the phosphorous oxychloride removed by distillation under reduced pressure. The last traces were removed by azeotroping with toluene (2×100 ml). The residue was dissolved in ethanol (5 ml) and 33% methylamine in ethanol (4.5 ml) was then added dropwise with cooling. The mixture was then stored at ambient temperature for 1.5 hours and the solvent was then removed by evaporation. The residue was partitioned between saturated sodium carbonate solution and methylene chloride. The organic layer was separated and the aqueous re-extracted with further methylene chloride (×2). The combined organic extracts were treated with decolourising charcoal and dried over anhydrous magnesium sulphate. After filtration and removal of the solvent by evaporation the residual solid was triturated with boiling n-hexane (3×100 ml). The solvent was evaporated to give a solid which was recrystallised from n-hexane. There was thus obtained 2,3,5,6-tetramethyl-4-methylimino-7-phenyl-3H,7H-pyrrolo-[2,3-d]pyrimidine (174 mg, 41.4% yield) as a white solid, m.p. 132°-133° C.; microanalysis, found: C, 72.8; H, 7.0; N, 20.2%; C$_{17}$H$_{20}$N$_4$ requires C, 72.8; H, 7.19; N, 20.0%; NMR: CDCl$_3$: 2.05–2.1(3H, s, CH$_3$), 2.3–2.4(6H, d, 2×CH$_3$-pyrrole), 3.5(3H, s, N—CH$_3$), 7.2–7.55(5H, complex, aromatic).

The starting material was prepared as follows:-

A mixture of 2,5,6-trimethyl-7-phenyl-3H,7H-pyrrolo-[2,3-d]pyrimidin-4-one (1.46 g, 5.8 mM) (N S Girgis et atl, Synthesis, 1985, p101-104). A mixture of potassium hydroxide flake (327 mg, 5.8 mM) and methyl iodide (0.54 ml, 8.7 mM) in ethanol (37 ml) was heated under reflux for 15 hours. A mixture of methyl iodide (0.5 ml) and potassium hydroxide flake (0.3 g) was added and the reaction mixture heated under reflux for a further 3 hours. The solvent was evaporated and the residual solid suspended in water. The solid was collected by filtration and washed with water to give 2,3,5,6-tetramethyl-7-phenyl-3H,7H-pyrrolo-[2,3-d]pyrimidin-4-one (1.21 g, 78.5% yield) as a light foam solid, m p 215°–217° C.; NMR: DMSO-$d_6$ 2.0–2.1(3H, s, CH$_3$), 2.3(3H, s, pyrrole CH$_3$), 2.4(3H, s, pyrrole- CH$_3$), 3.4–3.5(3H, s, N—CH$_3$), 7.3–7.6(5H, complex, aromatic).

EXAMPLES 4–7

The procedure described in Example 3 was repeated using 2,3,5,6-tetramethyl-7-phenyl-3H,7H-pyrrolo-[2,3,-d]pyrimidin-4-one and the appropriate substituted amine in place of methylamine. There was thus obtained the following compounds of formula I ($R^2=R^3=R^5=R^4$=methyl).

| Example | $R^1$ | Recryst solvent | M.Pt (°C.) | Yield (%) |
|---|---|---|---|---|
| 4 | H | Hexane | 207–209 | 26.8 |
| 5 | n-propyl | Hexane | 106–109 | 26.6 |
| 6 | ethyl | Hexane | 135–137 | 33.3 |
| 7 | n-hexyl | Hexane | 124–125 | 45.8 |

EXAMPLE 8

The procedure described in Example 3 was repeated using 3,5,6-trimethyl-7-phenyl-3H,7H-pyrrolo-[2,3-d]pyrimidin-4-one (in place of 2,3,5,6-tetramethyl-7-phenyl-3H,7H-pyrrolo-[2,3-d]pyrimidin-4-one) and ammonia (in place of methylamine). There was thus obtained 3,5,6-trimethyl-4-imino-7-phenyl-3H,7H-pyrrolo-[2,3-d]pyrimidine as a white solid m.p. 187°–188° C.; 40.2% yield; microanalysis, found: C, 71.4; H, 6.3; N, 22.5; $C_{15}H_{16}N_4$ requires C,71.4; H, 6.39; N, 22.2; NMR: CDCl$_3$: 2.5(3H, s, CH), 2.4(3H, s, CH$_3$), 3.5–3.6(3H, s, N-CH$_3$), 7.2–7.35(2H, complex, C—H and aromatic proton), 7.4–7.6(4H, complex, aromatic), N-H not observed.

The starting material was prepared as described in Example 3 by the alkylation with methyl iodide of 5,6-dimethyl-7-phenyl-3H,7H-pyrrolo-[2,3-d]pyrimidin-4-one (see US Patent 4,229,453). There was thus obtained 3,5,6-trimethyl-7-phenyl-3H-7H-pyrrolo-[2,3-d]pyrimidin-4-one (62.4% yield) m.p. 207°–208° C.; microanalysis, found: C, 71.0; H, 6.2; N, 16.3%; $C_{15}H_{15}N_3$ requires C, 71.1; H, 5.97; N, 16.6%; NMR: CDCl$_3$; 2.1(3H, s, CH$_3$), 2.4–2.5(3H, s, CH$_3$), 3.5–3.6(3H, s, N-CH$_3$), 7.25–7.6(5H, complex, aromatic), 7.7–7.8(1H, s, C-H).

EXAMPLE 9

The following illustrate representative pharmaceutical dosage forms containing a compound of formula I, or an alternative non-toxic salt thereof, which may be used for therapeutic or prophylactic purpose in humans:-

| (a) Tablet | mg/tablet |
|---|---|
| Compound X | 50 |
| Lactose Ph.Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (b) Capsule | mg/capsule |
|---|---|
| Compound X | 10 |
| Lactose Ph.Eur | 488.5 |
| Magnesium stearate | 1.5 |

"Compound X" stands for a typical compound of the formula I or an alternative non-toxic salt thereof such as is described in the preceding Example herein.

The above formulations may be obtained by conventional procedures well known in the pharmaceutical art. The tablets may be coated by conventional means, for example to modify dissolution/disintegration characteristics or improve palatability or stability. For example, a coating of cellulose acetate phthalate may be applied to the tablets to provide a formulation which predominantly releases the majority of the active ingredient in or near. the lower alimentary tract.

SCHEME A

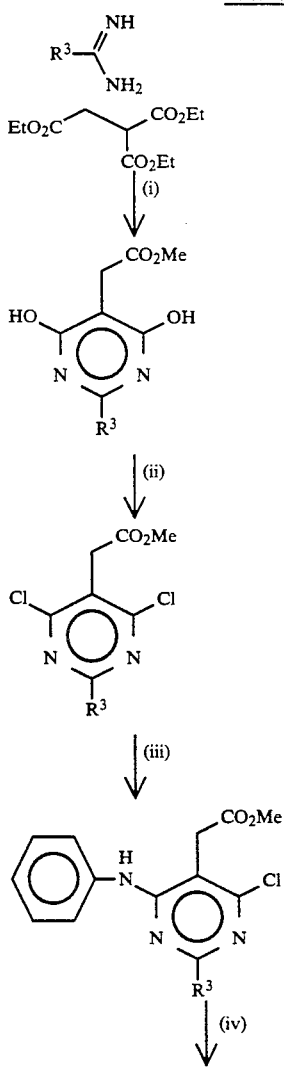

-continued
SCHEME A
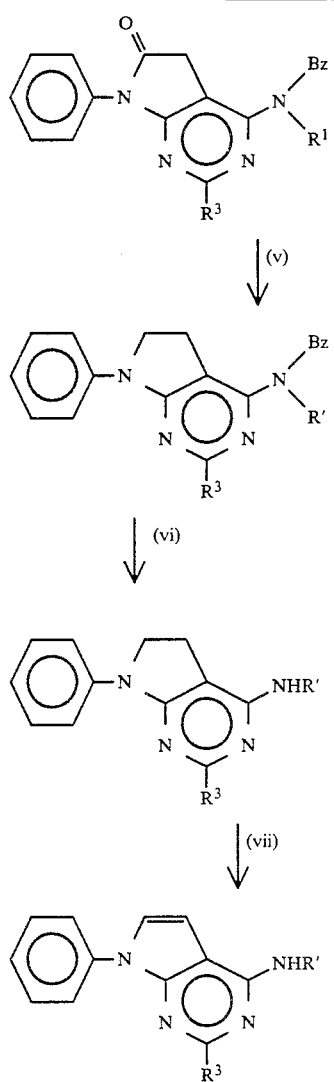
Reagents and conditions
(i) NaOMe, methanol, heat
(ii) POCl₃ (excess), reflux
(iii) aniline (appropriately substituted)
(iv) BZ NH, heat R¹
(v) IM BH₃.THF complex in THF
(vi) ammonium formate, 10% Pd/C, ethanol, reflux
(vii) 30% Pd/C, diphenyl ether, reflux
SCHEME B
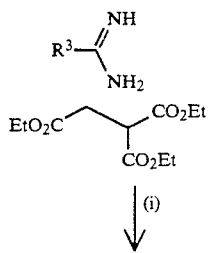
-continued
SCHEME B
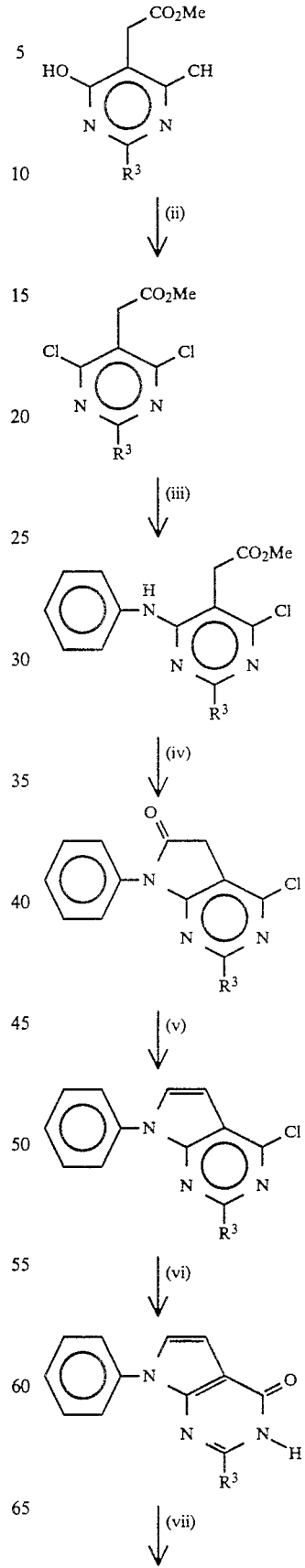

-continued
SCHEME B

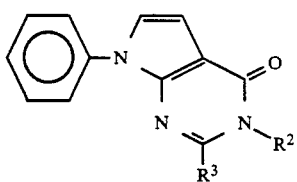

Reagents and conditions
(i) NaOME, methanol, heat
(ii) POCl$_3$ (excess), reflux
(iii) aniline (approximately substituted)
(iv) heat
(v) IM BH$_3$. THF complex, THF
(vi) 2NHCl, ethanol, reflux
(vii) KOH, ethanol, R$^2$I

CHEMICAL FORMULAE

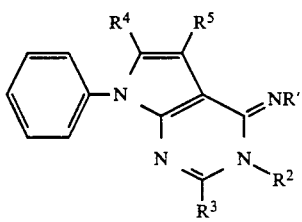

I

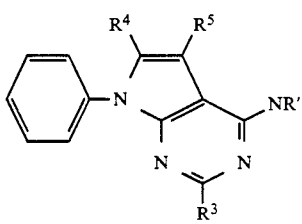

II

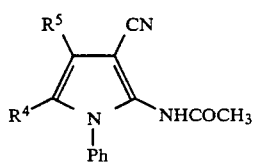

III

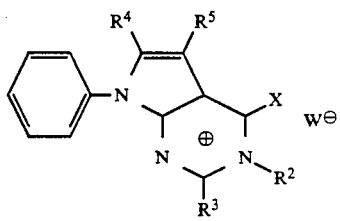

IV

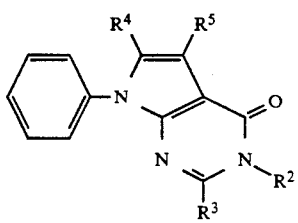

V

-continued
CHEMICAL FORMULAE

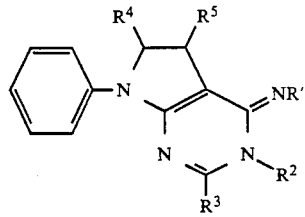

VI

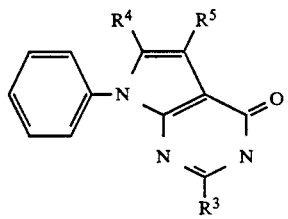

VII

I claim:
1. A compound of formula I or a pharmaceutically-acceptable salt thereof,

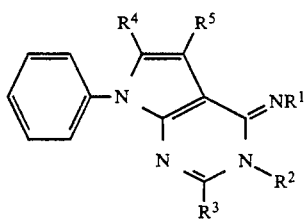

I wherein:
R$^1$ is hydrogen, (1–8C)alkyl or phenyl(1–4C)alkyl;
R$^2$ is (1–6C)alkyl, (3–6C)cycloalkyl or (3–6C)cycloalkyl(1–4C)alkyl;
R$^3$ is hydrogen, (1–6C)alkyl, phenyl (1–4C)alkyl, (3–6C)cycloalkyl, (3–6C)cycloalkyl(1–4C)alkyl, phenyl or (3–6C)alkenyl;
R$^4$ and R$^5$ are independently selected from hydrogen and (1–6C)alkyl; and wherein the phenyl ring shown in formula I and/or one or more of said phenyl moieties recited as R$^1$ or R$^3$ [or benzene moieties] may optionally be unsubstituted or substituted by one or more substituts independently selected from halogeno, (1–4C)alkyl, (3–6C)alkenyl, (1–4C)alkoxy, cyano, trifluoromethyl, mitro, carboxy, (1–4C)alkylamino, dialkylamino of up to six carbon atoms, (1–4C)alkythion, (1–4C)alkylsulphinyl, (1–4C)alkylsulphonyl and (1–4C)alkylenedioxy;
but excluding the compound in which R$^1$, R$^3$, R$^4$ and R$^5$ are each methyl, the phenyl ring is unsubstituted and R$^2$ is ethyl, and its pharmaceutically-acceptable salts.
2. A compound as claimed in claim 1 wherein:
R$^1$ is hydrogen, methyl, ethyl, propyl, isopropyl, butyl, isobutyl, sec-butyl, pentyl, hexyl, bensyl, 1-phenylethyl or 2-phenylethyl;
R$^2$ is methyl, ethyl, propyl, isopropyl, butyl, isobutyl, sec-butyl, cyclopropylethyl, cyclobutylmethyl, cyclobutylethyl, cyclopentylmethyl, cyclopentylethyl, cyclohexylmethyl, cyclohexylethyl, cyclopropyl, cyclobutyl, cyclopentyl or cyclohexyl,;
R$^3$ is hydrogen, methyl, ethyl, propyl, isopropyl, butyl, isobutyl, sec-butyl, benzyl, 1-phenylethyl, 2-phenylethyl, cyclopropyl, cyclobutyl, cyclopentyl, cyclohexyl, cyclopropylmethyl, cyclopropylethyl, cyclobutylmethyl, cyclobutylethyl, cyclopentylmethyl, cyclopentylethyl, cyclohexylmethyl, cyclohexylethyl, allyl, but-2-enyl, but-3-enyl, 2-methyl-2-propenyl, pentenyl or phenyl; $R^4$ and $R^5$ are independently selected from hydrogen, methyl, ethyl, propyl, isopropyl, butyl, isobutyl and sec-butyl; and wherein the phenyl ring shown in formula I and/or one or more of said phenyl moieties recited as $R^1$ or $R^3$ may optionally be unsubstituted or substituted by one or more substituents independently selected from fluoro, chloro, bromo, methyl, ethyl, propyl, allyl, 2-methyl-2-propenyl, methoxy, ethoxy, propoxy, cyano, trifluoromethyl, nitro, carboxy, methylamino, ethylamino, dimethylamino, diethylamino, methylthio, ethylthio, methylsulphinyl, ethylsulphinyl, methylsulphonyl, ethlsulphonyl, methylenedioxy, isopropylidenedioxy.

3. A compound as claimed in claim 1 wherein: $R^1$ is (1–6C)alkyl or benzyl; $R^2$ is (1–6C)alkyl, (3–6C)cycloalkyl(1–4C)alkyl, or benzyl; $R^3$ is (1–6C)alkyl; and wherein the phenyl ring and/or the phenyl moiety of the benzyl group is unsubstituted or is substituted by one or more substituents independently selected from halogeno, (1–4C)alkyl, (3–6C)alkenyl, (1–4C)alkoxy, cyano, trifluoromethyl, nitro, carboxy, (1–4C)alkylamino, dialkylamino of up to six carbon atoms, (1–4C)alkylthion, (1–4C)alkylsulphinyl, (1–4C)alkylsulphonyl and (1–4C)alkylenedioxy.

4. A compound as claimed in claim 1 or 2 wherein: $R^1$ is hydrogen or (1–6C)alkyl; $R^2$ is (1–4C)alkyl; $R^3$ is hydrogen or (1–4C)alkyl; $R^4$ and $R^5$ are independentendly selected from hydrogen and (1–4C)alkyl; and wherein the phenyl ring may optionally be unsubstituted or substituted by one or two substituents independently selected from halogeno, (1–4C)alkyl, and (1–4C)alkoxy.

5. A compound of formula I or a pharmaceutically-acceptable salt thereof, wherein:
$R^1$ is hydrogen, (1–8C)alkyl or phenyl(1–4C)alkyl;
$R^2$ is methyl;
$R^3$ is hydrogen, (1–6C)alkyl, phenyl(1–4C), (3–6C)cycloalkyl, (3–6C)cycloalkyl(1–4C)alkyl, phenyl or (3–6C)alkenyl; $R^4$ and $R^5$ are independently selected from hydrogen and (1–6C)alkyl; and wherein the phenyl ring shown in formula I and/or one or more of said phenyl moieties recited as $R^1$ or $R^3$ may optionally be unsubstituted or substituted by one or more substituents independently selected from halogen, (1–4C)alkyl, (3–6C)alkenyl, (1–4)alkoxy, cyano, trifluoromethyl, nitro, carboxy, (1–4C)alkylamino, dialkylamino of up to six carbon atoms, (1–4C)alkylthio, (1–4C)alkylsulphinyl, (1–4C)alkylsulphonyl and (1–4C)alkylenedioxy.

6. A compound as claimed in claim 5 wherein: $R^1$ is hydrogen, methyl, ethyl, propyl, isopropyl, butyl, isobutyl, sec-butyl, pentyl or hexyl;

$R^2$ is methyl, ethyl, propyl, isopropyl, butyl, isobutyl, sec-butyl;
$R^3$ is hydrogen, methyl, ethyl, propyl, isopropyl, butyl, isobutyl or sec-butyl; $R^4$ and $R^5$ are independently selected from hydrogen, methyl, ethyl, propyl, isopropyl, butyl, isobutyl and sec-butyl; and wherein the phenyl ring shown in formula I may optionally be unsubstituted or substituted by one or more substituents independently selected from fluoro, chloro, bromo, methyl, ethyl, propyl, methoxy, ethoxy or propoxy.

7. A compound as claimed in claim 1 which is selected from:
2,3-dimethyl-4-methylimino-7-phenyl-3H,7H-pyrrolo[2,3-d]pyrimidine;
2,3,5,6-tetramethyl-4-methylimino-7-phenyl-3H,7H-pyrrolo-[2,3-d]pyrimidine;
2,3,5,6-tetramethyl-4-imino-7-phenyl-3H, 7H-pyrrolo-[2,3-d]pyrimidine;
2,3,5,6-tetramethyl-4-n-propylimino-7-phenyl-3H,7H-pyrrolo-[2,3-d]pyrimidine;
2,3,5,6-tetramethyl-4-ethylimino-7-phenyl-3H,7H-pyrrolo-[2,3-d]pyrimidine;
2,3,5,6-tetramethyl-4-n-hexylimino-7-phenyl-3H,7H-pyrrolo-[2,3d]pyrimidine;
3,5,6-trimethyl-4-imino-7-phenyl-3H,7H-pyrrolo-[2,3-d]pyrimidine;

8. A compound as claimed in claim 1 which is in the form of a salt selected from chloride, bromide, iodide, sulphate, nitrate and trifluoracetate.

9. A pharmaceutical composition comprising a compound as claimed in claim 1 or claim 5, or a pharmaceutically-acceptable salt thereof, in association with a pharmaceutically-acceptable diluent or carrier.

10. A method of modulating the action of the sinoatrial node in a warm-blooded animal requiring such treatment which comprises administering to said animal an effective amount of a pharmacologically active agent comprising a compound of the formula I or a pharmaceutically-acceptable salt thereof, wherein:
$R^1$ is hydrogen, (1–8C)alkyl or phenyl(1–4C)alkyl;
$R^2$ is (1–6C)alkyl, phenyl, phenyl(1–4C)alkyl, (3–6C)cycloalkyl or (3–6C)cycloalkyl(1–4C)alkyl;
$R^3$ is hydrogen, (1–6C)alkyl, phenyl(1–4C)alkyl, (3–6C)cycloalkyl, (3–6C)cycloalkyl(1–4C)alkyl, phenyl or (3–6C)alkenyl;
$R^4$ and $R^5$ are independently selected from hydrogen and (1–6C)alkyl; and wherein the phenyl ring shown in formula I and/or one or more of said phenyl moieties recited as $R^1$ or $R^3$ may optionally be unsubstituted or substituted by one or more substituents independently selected from halogeno, (1–4C)alkyl, (3–6C)alkenyl, (1–4C)alkoxy, cyano, trifluoromethyl, nitro, carboxy, (1–4C)alkylamino, dialkylamino of up to six carbon atoms, (1–4C)alkythio, (1–4C)alkylsulphinyl, (1–4C)alkylsulphonyl and (1–4C)alkylenedioxy; but excluding the compound in which $R^1$, $R^3$, $R^4$ and $R^5$ are each methyl, the phenyl ring is unsubstituted and $R^2$ is ethyl, and its pharmaceutically-acceptable salts.

* * * * *